US004001724B2

United States Statutory Invention Registration [19]

[11] Reg. Number: H1724

[45] Published: Apr. 7, 1998

Ahr

[54] ABSORBENT ARTICLE HAVING MULTIPLE BACKSHEET MEMBERS

[76] Inventor: Nicholas Albert Ahr, 3736 Benhill Dr., Cincinnati, Ohio 45247

[21] Appl. No.: 566,213

[22] Filed: Dec. 1, 1995

[51] Int. Cl.[6] ..... A61F 13/15

[52] U.S. Cl. ..... 604/385.1

[58] Field of Search ..... 604/358, 378, 604/385.1, 385.2, 383

[56] References Cited

U.S. PATENT DOCUMENTS

| | | | |
|---|---|---|---|
| 2,837,095 | 6/1958 | Stevenson | 604/385.1 |
| 2,929,379 | 3/1960 | Poulsen . | |
| 3,367,334 | 2/1968 | Testa . | |
| 3,580,252 | 5/1971 | Delort . | |
| 4,094,316 | 6/1978 | Nathanson . | |
| 4,097,943 | 7/1978 | O'Connell . | |
| 4,161,176 | 7/1979 | Harris, II et al. . | |
| 4,405,310 | 9/1983 | Karami | 604/383 |
| 4,425,130 | 1/1984 | DesMarais | 604/389 |
| 4,576,597 | 3/1986 | Hlaban | 604/390 |
| 4,605,404 | 8/1986 | Sneider | 604/385 |
| 4,657,538 | 4/1987 | Becker et al. | 604/381 |
| 4,675,015 | 6/1987 | Brown | 604/385.1 |
| 4,765,477 | 8/1988 | Froidh et al. | 206/438 |
| 4,806,411 | 2/1989 | Mattingly, III et al. | 428/139 |
| 4,938,756 | 7/1990 | Salek | 604/368 |
| 4,964,857 | 10/1990 | Osborn | 604/395 |
| 4,968,312 | 11/1990 | Khan | 604/385.1 |
| 5,057,096 | 10/1991 | Faglione | 604/385.1 |
| 5,087,254 | 2/1992 | Davis et al. | 604/386 |
| 5,236,428 | 8/1993 | Zajackowski | 604/385.1 |
| 5,383,867 | 1/1995 | Klinger | 604/385.1 |
| 5,429,631 | 7/1995 | Grenier | 604/385.1 |
| 5,458,591 | 10/1995 | Roessler et al. | 604/364 |
| 5,460,624 | 10/1995 | Ahr et al. | 604/385.1 |
| 5,520,674 | 5/1996 | Lavon et al. | 604/385.1 |

FOREIGN PATENT DOCUMENTS

| | | | |
|---|---|---|---|
| WO 93/21878 | 11/1993 | WIPO | A61F 13/15 |
| WO 95/29655 | 11/1995 | WIPO | A61F 13/15 |

*Primary Examiner*—Charles T. Jordan
*Assistant Examiner*—Meena Chelliah

[57] ABSTRACT

The present invention provides an absorbent article including a first backsheethaving an aperture therein and a second backsheet releasably attached to the first backsheet and completely covering the aperture in the first backsheet. The second backsheet can be detached from the first backsheet, thus revealing the aperture in the first backsheet. The absorbent article can then be combined with an additional absorbent article where fluid acquired in the absorbent article can be transported to the underlying absorbent article to provide additional storage capacity.

6 Claims, 8 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLE HAVING MULTIPLE BACKSHEET MEMBERS

FIELD OF THE INVENTION

The present invention relates to absorbent articles, and more particularly, to absorbent articles having a portion of the backsheet being removable allowing the absorbent article to be combined with an additional absorbent article.

BACKGROUND OF THE INVENTION

Sanitary napkins configured for the absorption of bodily fluids are, of course, well-known. In their simplest form they comprise an absorbent element or core interposed between a liquid pervious body contacting element and a liquid impervious protective barrier. The absorbent element is, of course, intended to receive and contain menses and other vaginal discharges. The body contacting element (sometimes called a topsheet) is intended to provide more or less comfortable and dry-feeling contact with body surfaces while allowing free passage of fluids therethrough and into the absorbent core. The protective barrier (sometimes called a backsheet) is intended to prevent menses or other vaginal discharges which are expelled or escape from the absorbent core from soiling the user's undergarments.

In addition to the three functional elements mentioned above, sanitary napkins are generally provided with means for supporting the device adjacent the user's crotch area, even as the user moves, where it can most effectively perform its intended function. Traditionally, this support means has involved the use of waist encircling belts having suspenders depending from the front and rear thereof. The suspenders are of various designs and are provided with means of various designs for securing the sanitary napkin thereto.

More recently, sanitary napkins have been provided with an adhesive attachment means for securing the sanitary napkin to the crotch area of the user's undergarment. Elimination of the traditional belt is generally considered to be a definite advance in sanitary napkin technology.

While prior art sanitary napkins do perform their intended function, they are limited to the amount of fluid they can absorb by the capacity of the absorbent element. What is needed then is greater capacity offered by one or more absorbent articles. For example, the art is replete with bulky and often uncomfortable sanitary napkins which while providing increased fluid absorbent capacity do not offer comfortable manageability for a user. Ideally, sanitary napkins will be thin for comfort and manageability, but also provide adequate fluid absorbency. To these and other ends, applicant's inventive embodiment is directed.

SUMMARY OF THE INVENTION

The present invention provides an absorbent article which may be combined with an additional absorbent article to provide additional storage capacity. The absorbent article has a periphery comprising a pair of end edges and a pair of longitudinal edges, a body facing surface and a garment facing surface. The absorbent article comprises a liquid pervious topsheet, a first liquid impervious backsheet joined to the topsheet, the first backsheet has an aperture therein, and an absorbent core positioned between the topsheet and the first backsheet. Lastly, a removable liquid impervious second backsheet comprising a grasping member is releasably attached to the first backsheet and completely covers the aperture in the first backsheet.

BRIEF DESCRIPTION OF DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). As used herein, the term "sanitary napkin" or "napkin" refers to devices which absorb and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. It should be understood, however, that the present invention is also applicable to other feminine hygiene garments or catamenial pads such as pantiliners or other absorbent articles such as incontinence pads, and the like.

Figure 1:
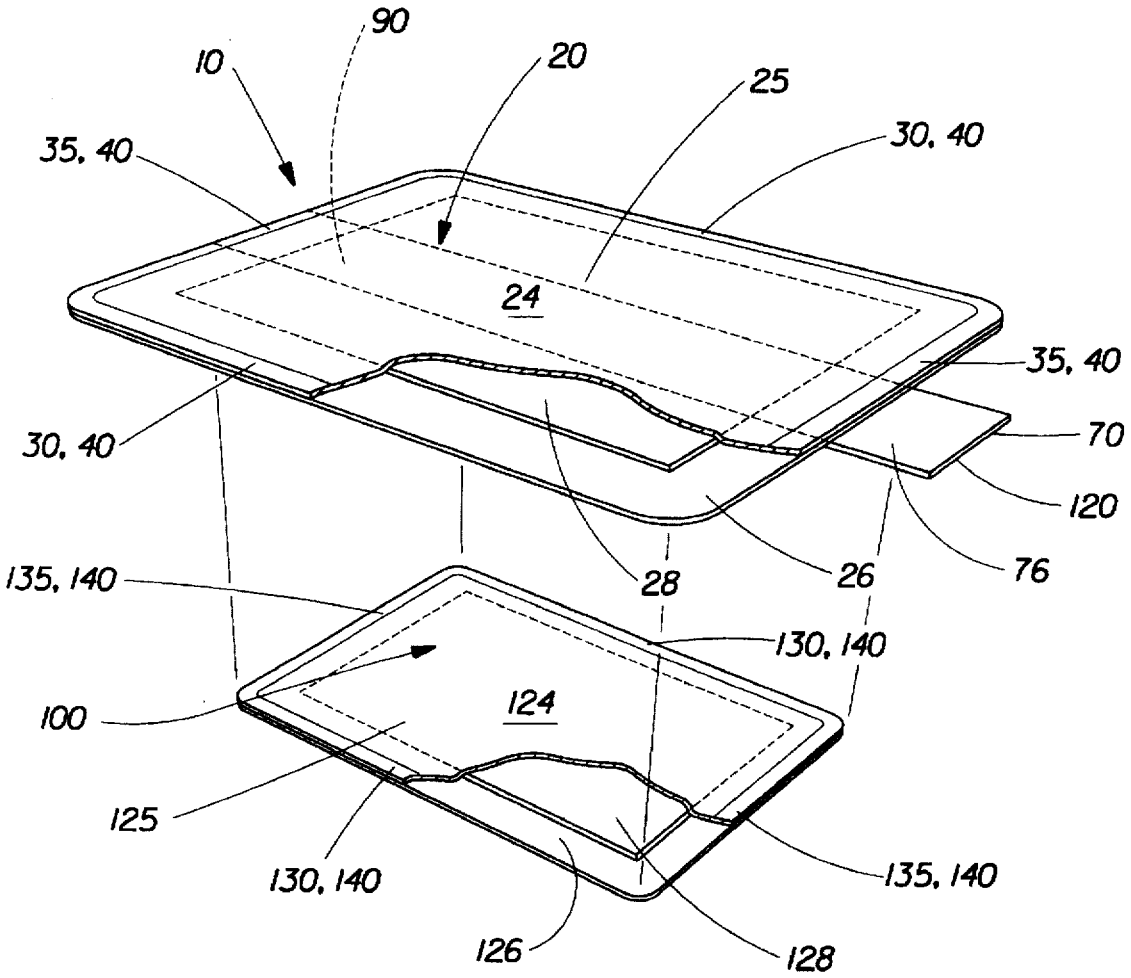
FIG. 1 is an exploded perspective view of the absorbent article of the present invention having portions cut away to reveal underlying structure.

FIG. 1 is an exploded perspective view of an absorbent article 10 of the present invention. The absorbent article 10 comprises the combination of a first, upper absorbent article 20 and a second, lower absorbent article 100. In the embodiment shown in FIG. 1, the first absorbent article 20 has length and width dimensions similar to those of the second absorbent article 100. However, in some situations it may be desirable to provide the first absorbent article 20 with different length and width dimensions than those of the second absorbent article 100.

The first absorbent article 20 is shown in FIG. 1 with portions of the structure being cut-away to more clearly show the construction of the first absorbent article 20. The first absorbent article 20 preferably comprises a liquid pervious topsheet 24, a first liquid impervious first backsheet 26 joined with the topsheet 24, a second backsheet 90 releasably attached to said first first backsheet 26 and an absorbent core 28 positioned between the topsheet 24 and the first backsheet 26.

Figure 2:
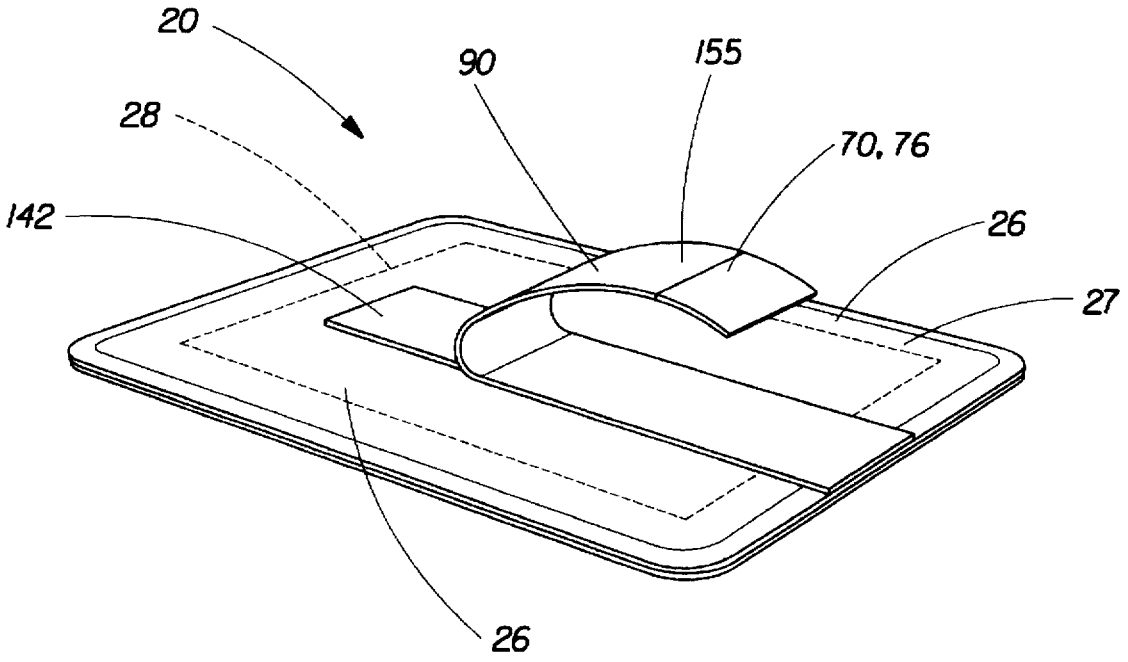
FIG. 2 is a perspective view of the first absorbent article having the second backsheet partially peeled away.
Figure 3:
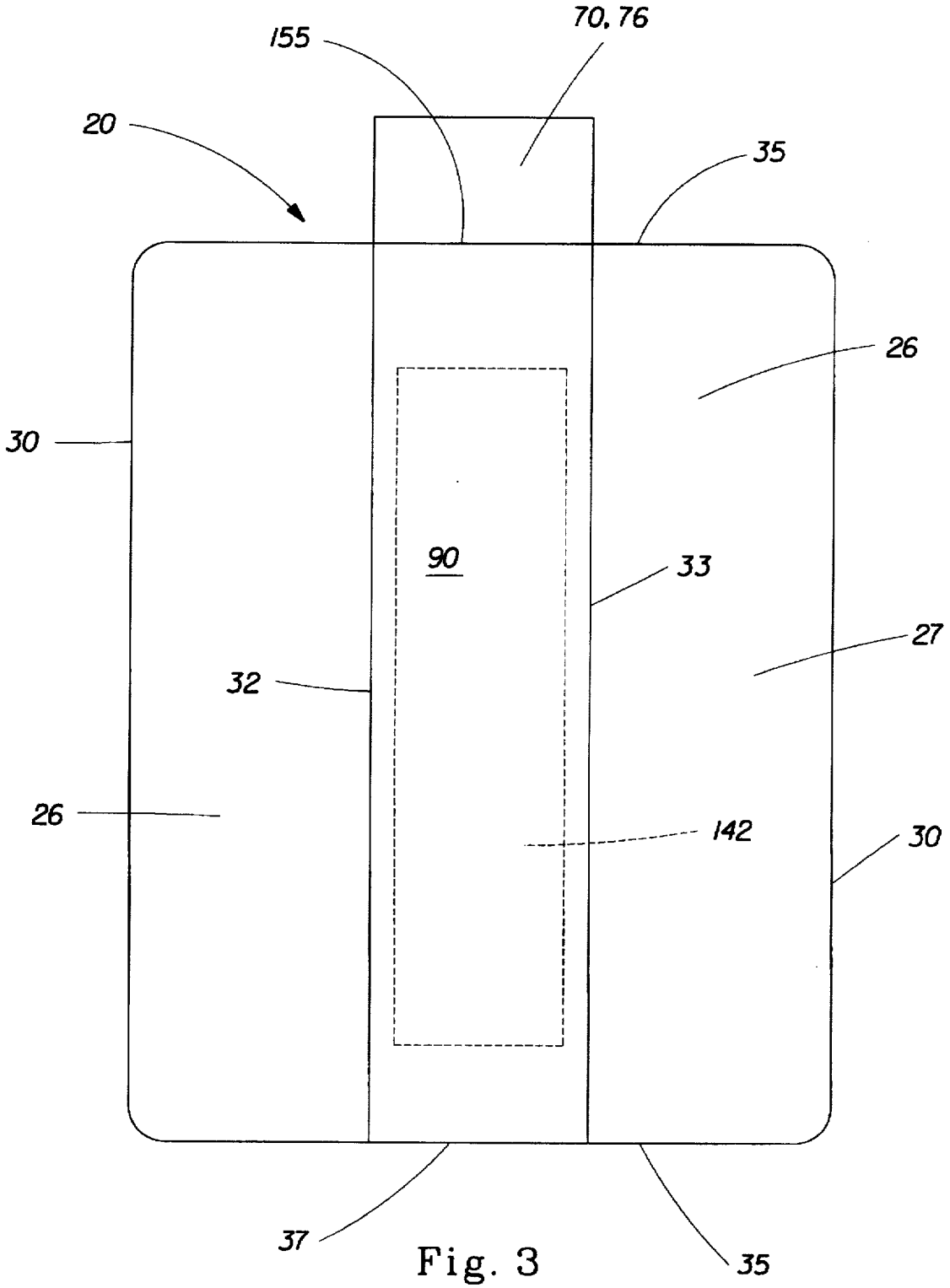
FIG. 3 is a plan view of the first absorbent article of the present invention as viewed from the garment facing surface.

The first absorbent article 20 has two surfaces, a body facing surface or "body surface" 25 and a garment facing surface 27 (shown in FIGS. 2 and 3). The body facing surface 25 is intended to be worn adjacent to the body of the wearer while the garment facing surface 27 is on the opposite side and is intended to be placed adjacent to the second absorbent article 100. FIG. 1 also shows that the first absorbent article 20 has a periphery 40 which comprises longitudinal edges 30 and end edges 35.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the first absorbent article 20 in which the topsheet 24 and the first backsheet 26 have length and width dimensions generally larger than those of the absorbent core 28. The topsheet 24 and the first backsheet 26 extend beyond the edges of the absorbent core 28 to form portions of the periphery 40.

The absorbent core 28 may be any absorbent means which is capable of absorbing or retaining liquids (e.g., menses and/or urine). As shown in FIG. 1 the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 28 may also be varied (e.g., the absorbent core 28 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 28 should, however, be compatible with the design loading and the intended use of the first absorbent article 20. Further, the size and absorbent capacity of the absorbent core 28 may be varied to accommodate different uses such as incontinence pads, pantiliners, regular sanitary napkins, or overnight sanitary napkins.

Most preferably, the absorbent core 28 comprises fluid distribution members comprising three basic components: chemically stiffened, twisted, and curled bulking fibers, high surface area fibers, and thermoplastic binder fibers. These fluid distribution members use a high surface area fiber to provide the fluid distribution member with capillary pressure (or suction). These high surface area fibers are generally small and highly conformable. They provide the substrate with capillary pressure well in excess of the capillary pressure found in the bulk-providing chemically stiffened, twisted, and curled fibers alone.

A preferred fiber for use in the absorbent core 28 is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen. Particularly suitable eucalyptus fibers include those of the *eucalyptus grandis* species. Exemplary fluid distribution members are described in U.S. patent application Ser. No. 08/382,817 filed Feb. 3, 1995, in the names of J. C. Horney and J. R. Noel, the disclosure of which is incorporated herein by reference.

Exemplary absorbent structures for use as the absorbent core 28 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The first backsheet 26 and the topsheet 24 are positioned adjacent the garment surface and the body surface, respectively, of the absorbent core 28 and are preferably joined thereto and to each other by attachment means (not shown) such as those well known in the art. For example, the first backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The first backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The first backsheet 26 prevents the exudates absorbed and contained in the absorbent core 28 from wetting articles which contact the absorbent articles described herein such as pants, pajamas and undergarments. The first backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Incorporated, of Terre Haute, Ind., under the designation XP-39385. The backsheet is preferably embossed and/or matte finished to provide a more clothlike appearance. Further, the first backsheet 26 may permit vapors to escape from the absorbent core 28 (i.e., breathable) while still preventing exudates from passing through the first backsheet 26.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

FIG. 2 is a perspective view of the first absorbent article 20 wherein the second backsheet 90 is partially removed from the first first backsheet 26 to reveal aperture 142 in first first backsheet 26. In the embodiment shown in FIG. 2, the absorbent core 28 is positioned immediately adjacent aperture 142 in first backsheet 26. Alternatively, other suitable materials which may be positioned adjacent to aperture 142 include an acquisition/distribution layer and/or any suitable material which will readily provide fluid transport from the first absorbent article 20 to the second absorbent article 100.

Referring again to FIG. 2, the second backsheet 90 has been partially removed from the first first backsheet 26 by grasping means 70 which preferably is a tab 76. The tab 76 is connected to the second backsheet 90 at juncture 155. Alternatively, the gasping member 70 may be an extension of the second backsheet 90.

FIG. 3 is a plan view of the absorbent article 20 of the present invention (as shown from the garment facing surface 27). The second backsheet 90 completely covers the aperture 142 in the first backsheet 26 and is secured to the first backsheet 26 with an adhesive 82 (shown in FIGS. 4 and 5). The adhesive 82 is positioned adjacent to the side edges 32 and 33, juncture 155, and end edge 37 of the second backsheet 90. Prior to removal of the second backsheet 90, the second backsheet 90 along with adhesive 82 seal the aperture 142 in the first backsheet 26.

Figure 4:
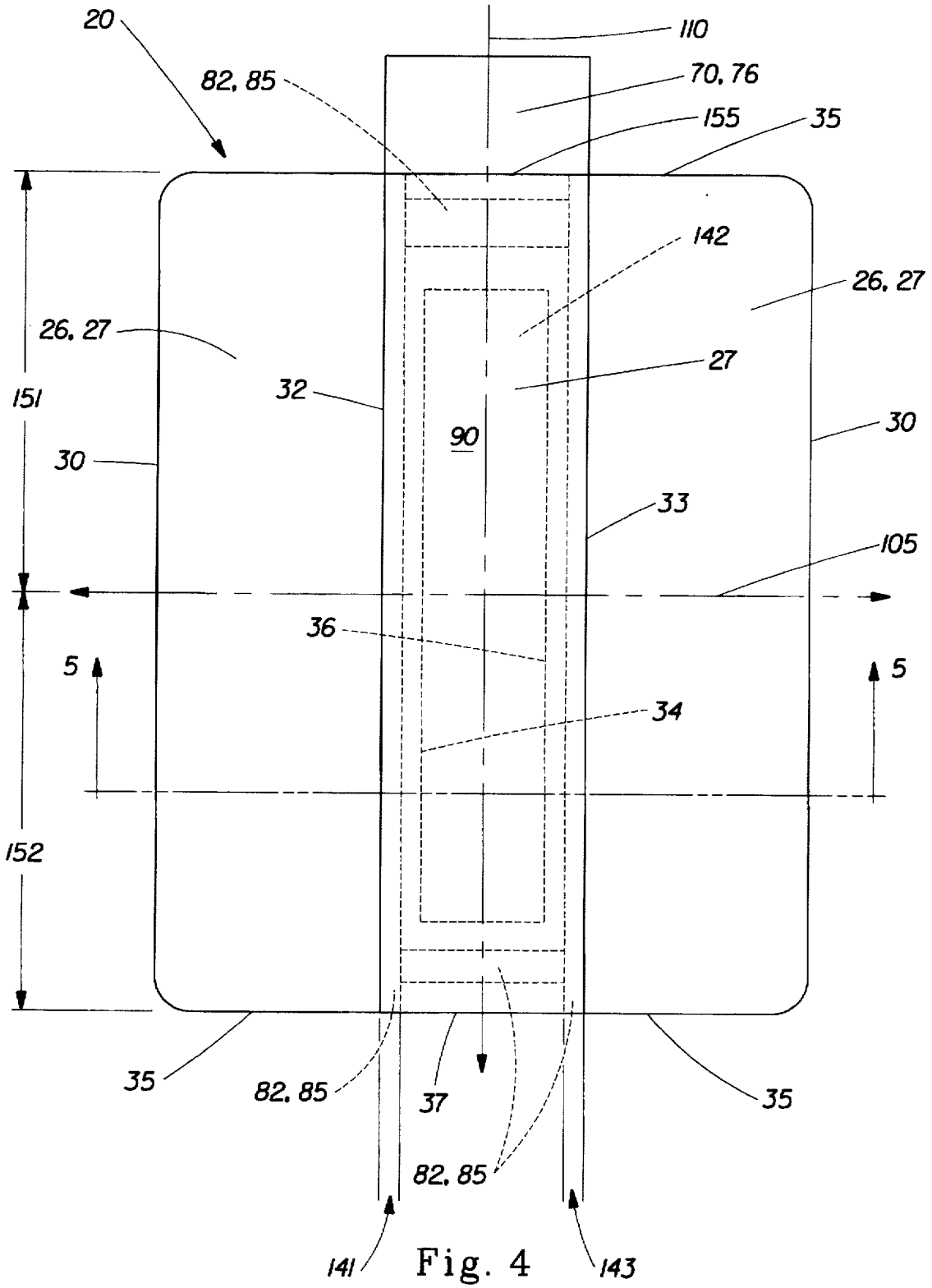
FIG. 4 is a more detailed plan view of the first absorbent article of FIG. 3.

FIG. 4, which is a more detailed depiction of the embodiment shown in FIG. 3, shows the garment facing surface 27 of the first first backsheet 26 and the second backsheet 90 which is preferably releasably attached to the first first backsheet 26 by an adhesive 82. Alternatively, the adhesive 82 can be attached to the garment surface 27 of the first first backsheet 26 of the first absorbent article 20, with a release means, most preferably being a release liner 85, being aligned with the adhesive 82 and attached to the second backsheet 90. In all cases where there is a release liner 85, it will be aligned with and receive substantially all of the adhesive 82.

The adhesive 82 is any one or more of several adhesives known in the art for use with absorbent articles and the components thereof. Adhesives which have been found to be satisfactory are manufactured by H. B. Fuller Company of St. Paul, Minn. under the designation HL-1258 of H-2031. Preferably, a release liner 85 is one of the following: BL30MG-A Silox E1/0 and BL30MG-A Silox 4P/O both of which are manufactured by the Akrosil Corporation of Menasha, Wis.

Preferably, the second backsheet 90 will have a first side edge 32 and a second side edge 33 which extend over and beyond the inner edges 34 and 36 of the aperture 142 in the first first backsheet 26 creating backsheet overlap portions 141 and 143. In a preferred embodiment, adhesive 82 located on the second backsheet 90 is spaced from the side edges 32 and 33. Preferably, release means 85 is aligned with and receives substantially all of the adhesive 82 and is attached to the garment surface 27 of the first first backsheet 26 at the first and second backsheet overlap portions 141 and 143, respectively. Also, the adhesive 82 may be positioned on the first backsheet 26 and the release liner 85 may be positioned on the second backsheet 90. FIG. 4 shows transverse axis 105 and longitudinal axis 110.

Figure 5:
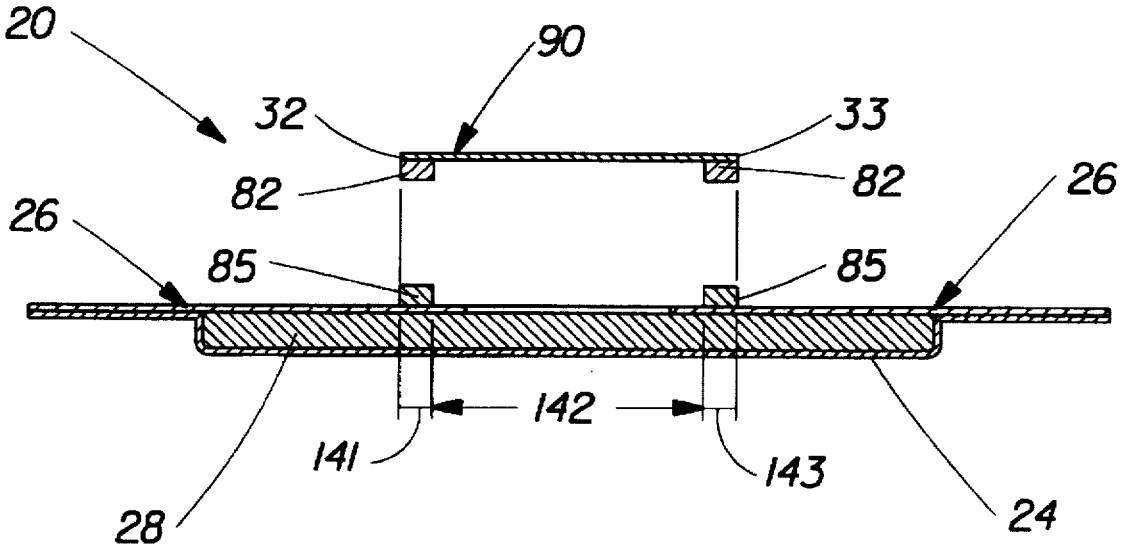
FIG. 5 is a cross-sectional view of the absorbent article of FIG. 4.

FIG. 5 is a cross-sectional view of the absorbent article 20 of FIG. 4. The first backsheet overlap zone 141 and the second backsheet overlap zone 143 are created when the second backsheet 90 is releasably attached to the first backsheet 26 to completely cover the aperture 142. Releasable attachment means 82 secured to the second backsheet 90 is preferably aligned with release means 85 on first backsheet 26.

Referring now to FIGS. 2 and 3, once the second backsheet 90 is removed, aperture 142 can reveal material within the absorbent article, such as the absorbent core, an acquisition/distribution layer (not shown), and/or any type of material that can transport fluid from the first absorbent article 20 to another absorbent article such as second absorbent article 100 shown in FIG. 1. While not wishing to be limited by any particular theory, such fluid transport (at saturation or on demand) can occur by varying capillary gradients from the first absorbent article 20 to the second absorbent article 100, wherein the second absorbent article 100 serves as a sink for transported fluid. In use, a user may remove the second backsheet 90 either before placement and use of the absorbent article in an undergarment or during use of the absorbent article, for example, when the first absorbent article becomes saturated and a need for more storage capacity thus arises. In the first instance, a user anticipating a "heavy flow" would remove the second backsheet 90 from first absorbent article 20 thus exposing aperture 142. At such removal, the user would then place the first absorbent article 20 onto the second absorbent article 100, and then place the combined absorbent article 10 into his/her undergarment. In the second instance, a user would remove the backsheet 90 upon saturation or near saturation of the absorbent article 20 without discarding the first absorbent article 20. At such removal, the second absorbent article 100 becomes a sink for transported fluid from the first absorbent article 20. Thus, in both instances the second absorbent article 100 acts as a storage sink to fluid transported from the first absorbent article 20. The storage capacity of the second absorbent article is activated upon removal of the second backsheet 90.

Figure 6:
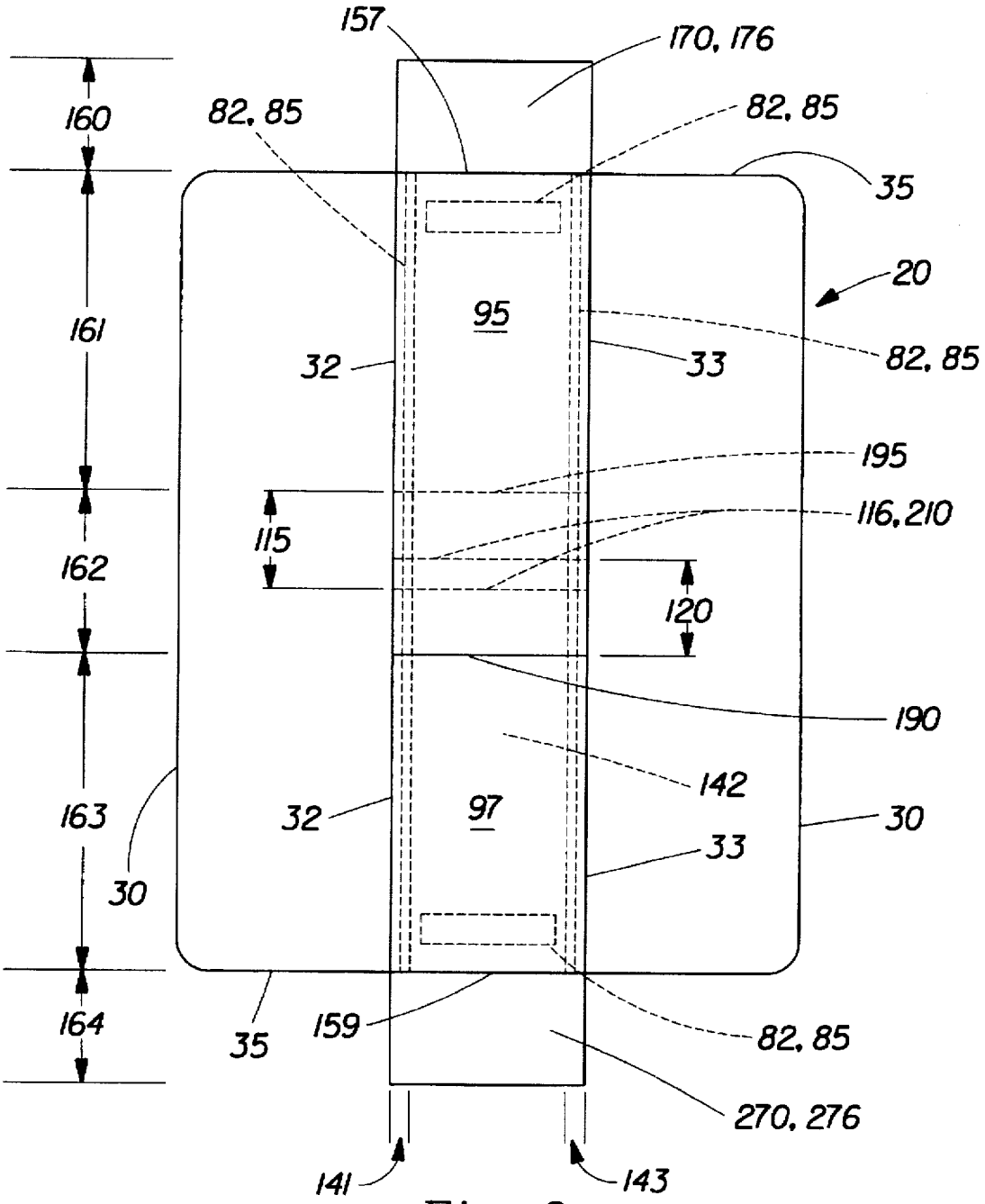
FIG. 6 is a plan view of an alternative embodiment of the first absorbent article of the present invention.

FIG. 6 shows an alternative embodiment of the present invention in which the first absorbent article 20 comprises a first grasping zone 160, a second grasping zone 164, a second backsheet 95, a third backsheet 97, a frontal zone 161, an overlap zone 162, and an end zone 163. Furthermore, the first absorbent article 20 comprises a first backsheet overlap zone 141, an aperture 142, and a second backsheet overlap zone 143. The second and third backsheets 95 and 97 are overlapped and releasably attached to one-another by overlap attachment means 210, most preferably being an adhesive, which extends from one longitudinal edge 32 to the other longitudinal edge 33 of the second backsheet 95, the overlap attachment means 210 being thus located on the second backsheet 95. Preferably, an overlap release means 116 is aligned with and located opposite from the overlap attachment means 210, and thus is placed on the garment facing surface of the third backsheet 97.

Most preferably, the first and second grasping members 170 and 270 are first and second tabs 176 and 276, respectively. The first tab 176 is joined to the second backsheet 95 at the first juncture 157. The second tab 276 is joined to the third backsheet 97 at the second juncture 159. Each tab extends from each respective juncture outwardly from the end edges 35 of the first absorbent article 20.

A user, according to his/her preferences may remove the second and third backsheets 95 and 97, respectively by using the first and second tabs 176 and 276. At removal, a user grasps the first tab 176 with one hand and the second tab 276 with the other hand. Then, a user pulls the first tab 176 in a direction generally parallel to the longitudinal axis 110 (shown in FIG. 4) away from the end edge 35 adjacent to the first juncture 157 and concurrently pulls the second tab 276 in a direction generally parallel to the longitudinal axis 110 away from the end edge 35 adjacent to the second juncture 159. The result is a removal of the second and third backsheets 95 and 97 from one-another and from the garment surface 27 of the first backsheet 26 of the first absorbent article 20, thus revealing aperture 142 whereby absorbed fluid and/or exudates from the first absorbent article 20 can, by differing capillary gradients, be transported to a second absorbent article.

Figure 7:
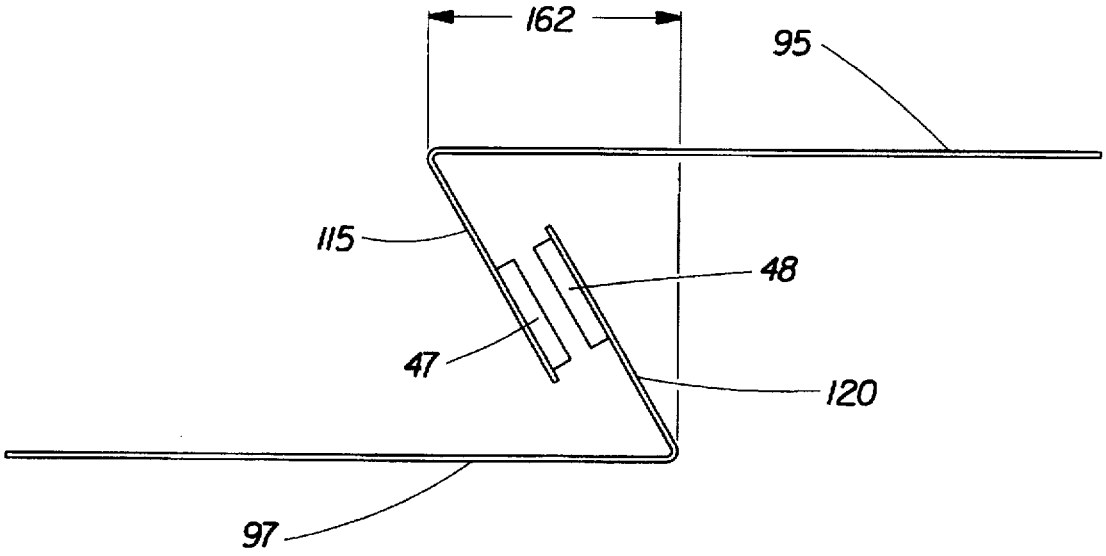
FIG. 7 is a side view of the fold embodiment of the first absorbent article of the present invention.

FIG. 7 discloses an alternative embodiment in which the overlap zone 162 comprises fold 115 in the second backsheet 95 and fold 120 in the third backsheet 97 which are releasably attached to one-another. Most preferably, this releasable attachment comes by fold attachment means 48 being aligned with and at least substantially received by fold receiving means 47. As shown, the fold receiving means 47 is located on fold 115. The fold attachment means 48 and fold receiving means 47 extend from one longitudinal edge 32 to the other longitudinal edge 33 (shown in FIG. 6), thus offering a seal to prevent fluid leakage before exposure of the aperture 142.

Most preferably, the fold attachment means 48 is an adhesive of the type disclosed herein for releasable attachment means 82. The fold receiving means 47 is a release liner of the type disclosed herein for receiving means 85. The fold attachment and receiving means 48 and 47, respectively are of a mechanical fastener type; e.g., hook and loop fasteners. Examples of such fasteners include those of mechanical closure systems disclosed in U.S. Pat. No. 4,869,724 issued to Scripps on Sep. 9, 1989; U.S. Pat. No. 4,848,815 issued to Scripps on Jul. 11, 1989 and the two-point securement system described in U.S. Pat. No. 5,242,436 issued to Weil, Buell, Clear and Falcone on Sep. 7, 1993 each of which are incorporated herein by reference.

Figure 8:
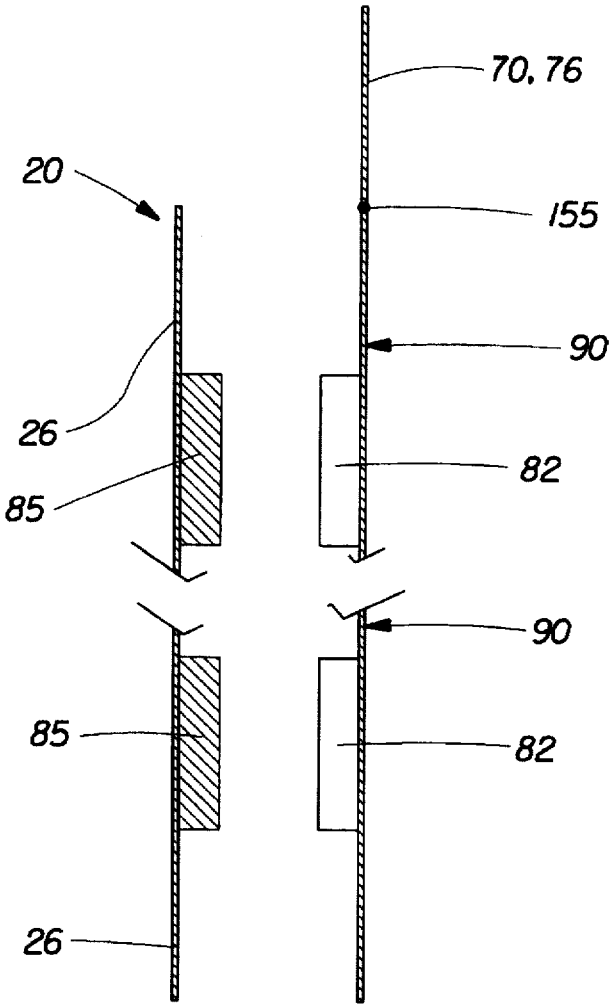
FIG. 8 is a fragmented cross-sectional view of an embodiment of the first absorbent article of the present invention.

FIG. 8 discloses a cross-sectional view of fragmented portions of the second backsheet 90 with releasable attachment means 82 aligned with receiving means 85 that are attached to the garment means 27 of the first backsheet 26. As shown, grasping member 70 (preferably, tab 76) is joined to second backsheet 90 at juncture 155.

In a preferred embodiment, first absorbent article 20 comprises adhesive attachment means 82 positioned parallel to the transverse axis 105 (shown in FIG. 4), in the frontal zone 151 and also, in the end zone 152. Release means 85 are aligned with and positioned opposite to the adhesive means 82. Most preferably, the adhesive attachment means 82 and release means 85 extend from the first liner 32 to the second edge 33 which results in an adhesive/liner seals in the transverse direction and in the frontal and end zones 151 and 152. Also preferably, adhesive attachment means 82 and release means 85 extend in the longitudinal direction from juncture 155 down to second backsheet edge 37 (or juncture 157 to juncture 159 for the embodiment in FIG. 2), one adhesive attachment means 82 being within the first backsheet overlap zone 141 and another being within the second backsheet overlap zone 143. As a result of this configuration of adhesive attachment means 82 being aligned with and positioned opposite to release means 85, a continuous seal between the second backsheet 90 and the first backsheet 26 to block out any fluid escape prior to the release of the second backsheet 90.

Figure 9:
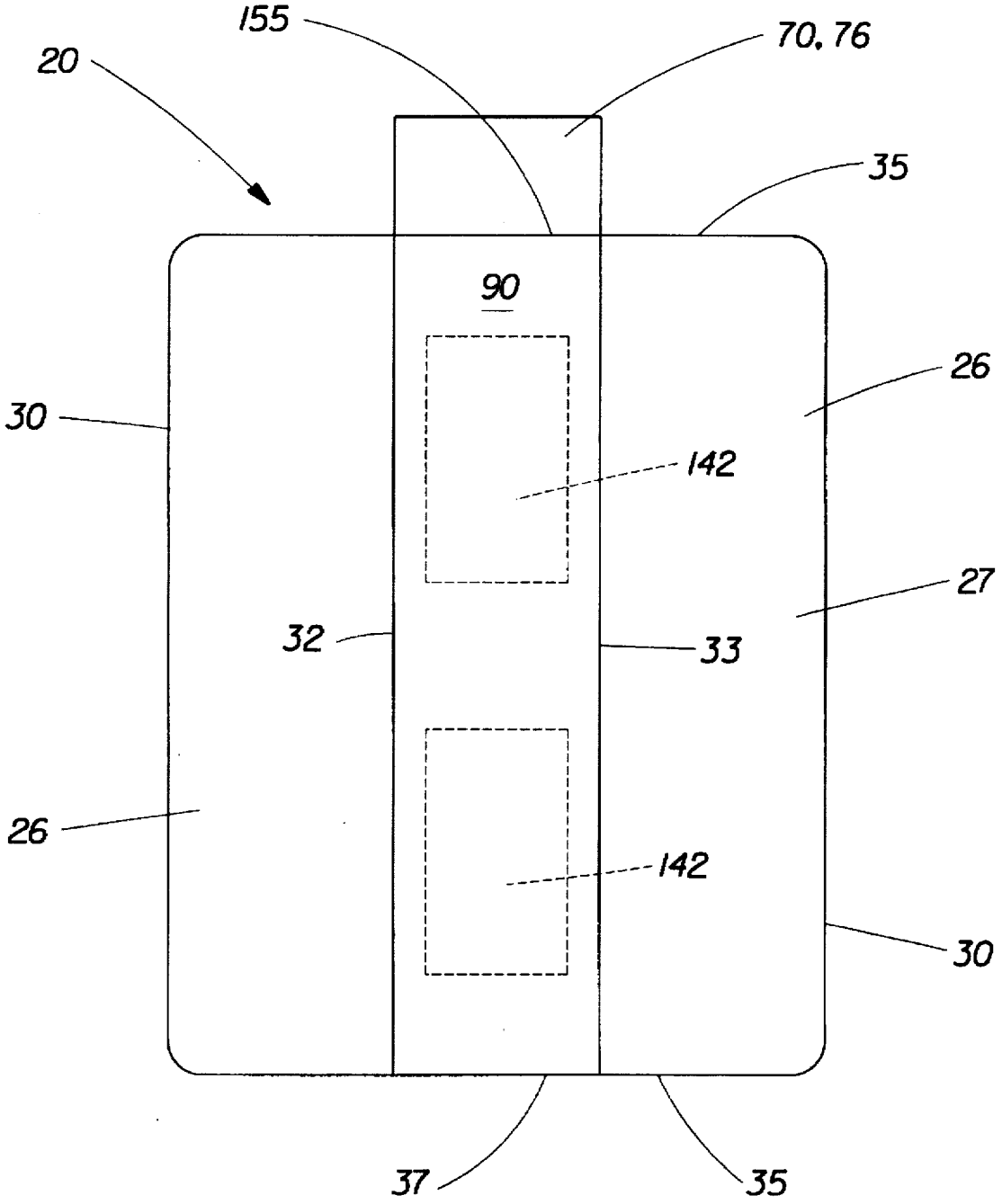
FIG. 9 is a plan view of an alternative embodiment of the first absorbent article of the present invention.

Referring now to FIG. 9, there is shown another embodiment of the first absorbent article of the present invention. First backsheet 26 has a plurality of apertures 142. In the embodiment shown in FIG. 9, first backsheet 26 contains two apertures 142 which are completely covered by the second backsheet 90. In other embodiments, it may be desirable to provide the first backsheet 26 with multiple apertures, for example, three, five, ten or more apertures. Once the second and/or third backsheets have been removed, depending of course on which embodiment is selected, more than one aperture is revealed. That is, there may be at least one division between adjacent apertures, a division being any material which distinguishes one aperture from another.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a periphery comprising a pair of end edges and a pair of longitudinal edges, a body facing surface and a garment facing surface, said absorbent article comprising:

a liquid pervious topsheet;

a first liquid impervious backsheet joined to said topsheet, said first backsheet having an aperture therein;

an absorbent core positioned between said topsheet and said first backsheet;

a removable liquid impervious second backsheet releasably attached to said first backsheet, said second backsheet partially covering said aperture in said first backsheet, said second backsheet comprising a grasping member; and a removable liquid impervious third backsheet releasably attached to said first backsheet and said second backsheet, said third backsheet at least partially covering said aperture in said first backsheet.

2. The absorbent article of claim 1 wherein said first backsheet comprises a plurality of apertures, said apertures being completely covered by said second and third backsheets.

3. The absorbent article of claim 1 wherein said first backsheet is releasably attached to said second backsheet and said third backsheet by an adhesive.

4. The absorbent article of claim 1 wherein said second backsheet is releasably attached to said third backsheet by an adhesive.

5. The absorbent article of claim 1 wherein said first backsheet is relesably attached to said second and said third backsheets by a plurality of hooks and a plurality of loops.

6. The absorbent article of claim 1 wherein said second backsheet and said third backsheet are releasably attached to one-another by a plurality of hooks and a plurality of loops.

* * * * *